United States Patent [19]

Cuming

[11] Patent Number: 4,513,608
[45] Date of Patent: Apr. 30, 1985

[54] MOISTURE SENSING AND CONTROL DEVICE

[76] Inventor: Kenneth J. Cuming, 68 Robinson Rd., Hawthorn, Victoria, Australia

[21] Appl. No.: 440,474

[22] Filed: Nov. 9, 1982

[30] Foreign Application Priority Data

Nov. 10, 1981 [AU] Australia .................. PF1504/81

[51] Int. Cl.$^3$ .................. G01R 27/20; G01N 27/12
[52] U.S. Cl. .................................. 73/73; 323/363; 323/365; 324/65 P
[58] Field of Search .............. 73/73; 338/34, 35; 324/65 P, 65 R; 323/363, 365, 366

[56] References Cited

U.S. PATENT DOCUMENTS

| | | | |
|---|---|---|---|
| 2,636,962 | 4/1953 | Bouyoucos | 338/34 |
| 2,729,099 | 1/1956 | Rosenthal | 73/73 |
| 2,740,032 | 3/1956 | Bouyoucos | 338/34 |
| 2,812,976 | 11/1957 | Hasenkamp | 73/73 |
| 2,941,174 | 6/1960 | Richards | 338/35 |
| 3,376,501 | 4/1968 | Peranio | 324/450 |
| 3,508,148 | 4/1970 | Enfield | 324/65 R |
| 3,782,179 | 1/1974 | Richards | 73/73 |
| 4,137,931 | 2/1979 | Hasenbeck | 73/73 |
| 4,321,577 | 3/1982 | Carlson | 338/35 |

FOREIGN PATENT DOCUMENTS 0779871 11/1980 U.S.S.R. .................. 73/73

Primary Examiner—Richard R. Stearns
Assistant Examiner—W. Morris Worth
Attorney, Agent, or Firm—Bell, Seltzer, Park & Gibson

[57] ABSTRACT

A moisture sensing element is provided and is constructed of a body having therein a first zone formed of porous material with a first range of pore size having a first mean pore size and a second zone formed of a porous material with a second range of pore size having a second mean pore size such that in use the body is located within a desired soil area under surveillance whereby both the first and second zones are placed in hydraulic conduction with the desired soil area. The first mean pore size is substantially greater than the second mean pore size such that the second zone will remain hydrated when the first zone is becoming dehydrated. Electrode elements are associated with each of the first and second zones in spaced relation and define therebetween respective electric current flow paths through each of the first and second zones for sensing an electrical property of each of the zones. The control devices further include a magnetic isolating device for electrically isolating respective pairs of electrode elements.

14 Claims, 6 Drawing Figures

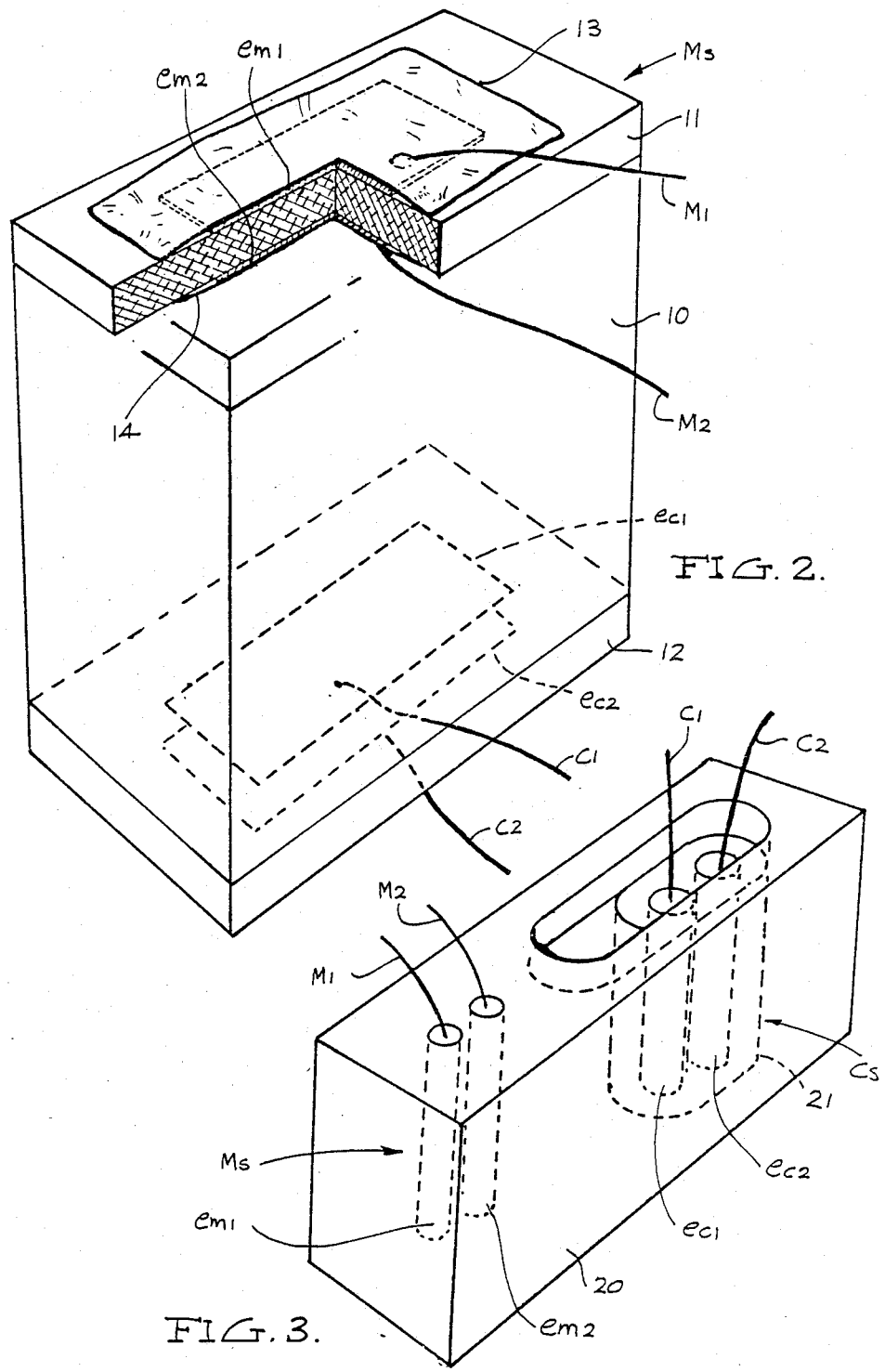

MOISTURE SENSING AND CONTROL DEVICE

The present invention relates to apparatus for sensing soil moisture and for providing a moisture level indication and/or a signal whereby other functions can be controlled such as water application to a particular area of soil may be conveniently controlled. The invention is particularly aimed at providing means whereby there can be established:

(1) an optimum root environment for plants,
(2) a minimal usage of water,
(3) a control on the leeching of solubles from the soil area, and
(4) a fully automatic control of watering systems, and
(5) a moisture sensing monitor and/or control means for other purposes.

To a quite significant extent, water application for plant or other agricultural cultivation purposes, has conventionally been by trial and error whether in commercial or domestic situations. The primary reason for this is that there has not been available any simple and reasonably accurate equipment which could be used by the person applying the water whereby a reliable measurement or indication of moisture content could be established. Relatively complicated and expensive laboratory equipment has of course been available but this is not found to be feasible for use by water users because of the complication and other practical considerations.

There has therefore always been an obvious need to have a simple and accurate device which is operable in the field and which will provide a substantially immediate soil moisture content indication to prevent conditions of either overwatering or under watering. Such a device would naturally be of substantial advantage in irrigation of dry land areas where over water usage should be prevented. Overwatering is also of particular concern where exclusion of oxygen from the root areas can be very detrimental to some plants in some soils. Moreover, overwatering can cause excessive seepage such that fertilizer, other soil nutrients and salts can be leeched from the soil and this will also have the substantial detrimental effect of contaminating tail water causing salinity contamination downstream.

There have, over a number of years, been numerous proposals for a simple and effective soil moisture level gauging device capable of reliable and effective field operation. A number of these proposals have been based on the realization that electrical resistance can vary in some relationship with the moisture content. To this end, several moisture sensing devices have been proposed comprising two or more spaced electrodes with a porous medium therebetween, they being free to absorb moisture from a soil area being examined and the electrodes being connected into a suitable control circuit to measure the change in electrical resistance across the porous medium as a result of changing moisture levels absorbed thereby. Typical of such devices are disclosed in U.S. Pat. Nos. 2,636,962, 2,729,099, 2,740,032 and 2,941,174.

Unfortunately, devices of the aforementioned kind have not proved to be satisfactory due to unreliable operation. The reasons for their lack of reliability are believed to be due to leaching of buffer zones in some cases and otherwise a number of factors including the substantial changes that can occur in the conductivity of the soil moisture resulting from a variation in solubles such as salts which can vary markedly from area to area and with conditions in the same area such as resulting from the application of fertilizer and other ion producing nutrients. Also stray electrical currents which can substantially affect readings. Other factors will be apparent from the following description.

It will be understood therefore, that the objective of the present invention is to provide a reliable device capable of sensing moisture content in a soil area and to be able to use this information to provide a moisture level indication or alternatively to control apparatus for supplying water to the area under surveillance. It is of course preferred that the device according to the invention be capable of ensuring roots have an optimum balance of oxygen and moisture while minimizing water usage, leeching and tail water contamination.

To achieve this objective, careful consideration was given to the factors involved in the soil structure including its nature and the method of soil hydration and dehydration. Normal soil consists of a wide range of particle sizes and shapes which, when consolidated, produce a range of connecting pore sizes in between the soil particles. As the soil is being dehydrated, the larger pore sizes having a lower matric tension become evacuated first. Progressively, higher tensions are required to dehydrate as the size of those pores remaining hydrated becomes smaller and smaller.

As the roots of plants must exert tension to draw moisture from the pores in the soil and as this tension must increase as the size of those pores remaining hydrated decreases, then sensing of some relationship such as soil tension would provide a closely related sensing of root stress in a plant system and as such would provide a superior criteria for irrigation control or other soil moisture related decisions.

Accordingly, the sensing element of the present invention provides in part, a structure which includes a porous material having suitable pore sizes which can be placed in hydraulic conduction with the soil under surveillance. The sensing element also includes means enabling measuring of the electrical conductivity to which a relationship to moisture content can be established. However, as will be appreciated from the foregoing, this relationship can vary dramatically due to the major changes in the specific conductivity of the moisture absorbed into the pores of the porous material, as can normally be expected in agricultural soils.

According to the present invention there is provided a sensing element comprising material(s) having a first zone formed of porous material with a first range of pore sizes having a first mean pore size and a second zone formed of porous material with a second range of pore sizes having a second mean pore size such that in use both said first and second zones are placed in hydraulic conduction with a desired soil area under surveillance, said first mean pore size being substantially greater than said second mean pore size such that the second zone will remain hydrated when the first zone is becoming dehydrated, and control means associated with each of said first and second zones such that an electrical property of said zones is sensed thereby.

The electrical means may advantageously include a pair of electrodes associated with each of said zones. The zones may be formed from the same type of material, or alternatively, could be formed from materials of different types. The zones may be formed by porous ceramic materials, however, other materials are also suitable.

In embodiments of the present invention, the pores in at least one of the first and second zones are controlled in size such that they are substantially uniform in size, that is, they do not markedly differ from the mean pore size. Preferably, this is arranged at least in the second zone, or in both zones. By specific control of the pore sizes within the porous material(s), the relationship between the matric tension and the degree of hydration of the respective medium can be controlled.

The relationship between mean diameter of the pores and the matric tension has been empirically established for porous ceramic materials. With reasonable accuracy the pore size of the zones are selected in accordance with the following formula:

$$Pm = K/Tm$$

where K is a constant for the material and the construction concerned, Tm is the matric tension and Pm is the mean pore diameter. Thus, a desired mean pore size can be established by selecting a matric tension value adequate that will maintain healthy plant growth with minimal water usage. The pore sizes of the first zone are selected to obtain the desired tension conductivity relationship for the application, the pore size for the second zone being selected to ensure that they remain hydrated within the working range of the device.

Conveniently, electrical connections to the first and second porous zones can be achieved by connecting circuit areas to the pair of electrodes implanted in each said zone. As a result of this construction, the impedance through each set of electrodes can be sensed, and the impedance of the set in the second porous zone which remains hydrated can be used to compensate the differential signal from the other set for changes in the specific conductivity and other variations of the electrolyte (the soil moisture).

In order to overcome the problems caused by relatively high impedances involved and insulation difficulties, it is preferred that electrical isolation of the sensing element from control circuits for the device be achieved. This may be achieved by magnetic coupling of the sensing element employing a transformer arrangement. A transformer means may be provided for each pair of electrodes with the respective electrodes being connected to the respective secondary windings of the transformer means. Consequently, when the primary windings of the respective transformer means are excited by an alternating current, their impedances vary in a predetermined relationship with changes in the impedances of the electrodes on their respective secondary windings. The primary windings of the respective transformer means may be connected in the adjacent arms of an electrical bridge whereby an electrolyte (soil moisture) compensated tension related signal is provided to indicate, upon suitable calibration, a moisture level, or alternatively to provide a means for water supply control.

In accordance with a further preferred aspect of the present invention there is provided a sensing element comprising a structure having a first zone formed of porous material of a first substantially uniform pore size and a second zone formed of porous material of a second substantially uniform pore size such that in use both said first and second zones are placed in hydraulic conduction with a desired soil area under surveillance, said first pore size being substantially greater than said second pore size whereby the second zone will remain hydrated when the first zone is becoming dehydrated, a first pair of electrode means in electrical conduction with said first zone, a second pair of electrode means in electrical conduction with said second zone, and electrical sensing means connected with said electrode means arranged to sense the conductivity of each of said first and second zones.

Several preferred embodiments of the present invention are hereinafter described with reference to the accompanying drawings. In the drawings:

FIG. 1b is a cross-sectional view taken along line A—A of FIG. 1a;

FIG. 1c is a cross-sectional view taken along line B—B of FIG. 1a;

FIG. 2 is a schematic perspective view partially cut away showing an alternative construction for the sensing element;

FIG. 3 is a schematic perspective view showing a further alternative construction for the sensing element.

Figure 1A:
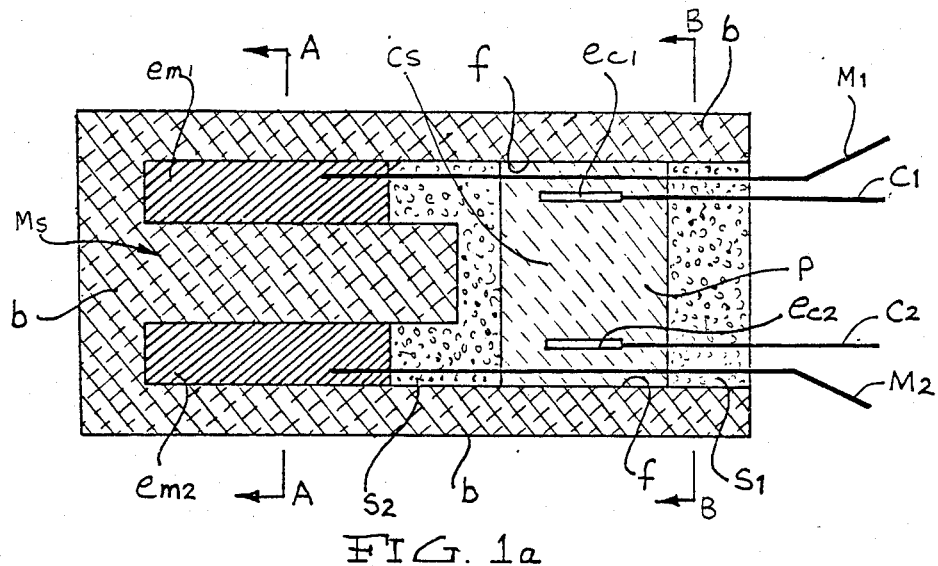
FIG. 1a is a longitudinal cross-sectional schematic view of a first preferred embodiment of a sensing element according to the present invention.
Figure 1B:
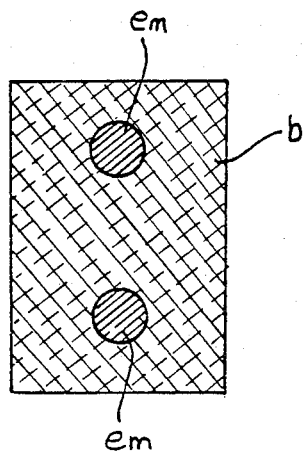
Figure 1C:
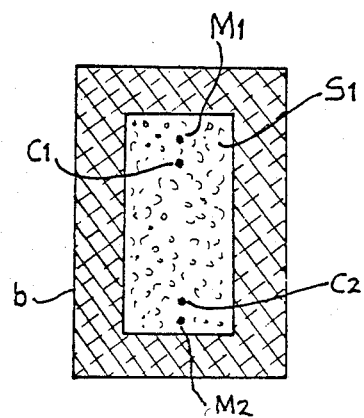
Figure 4:
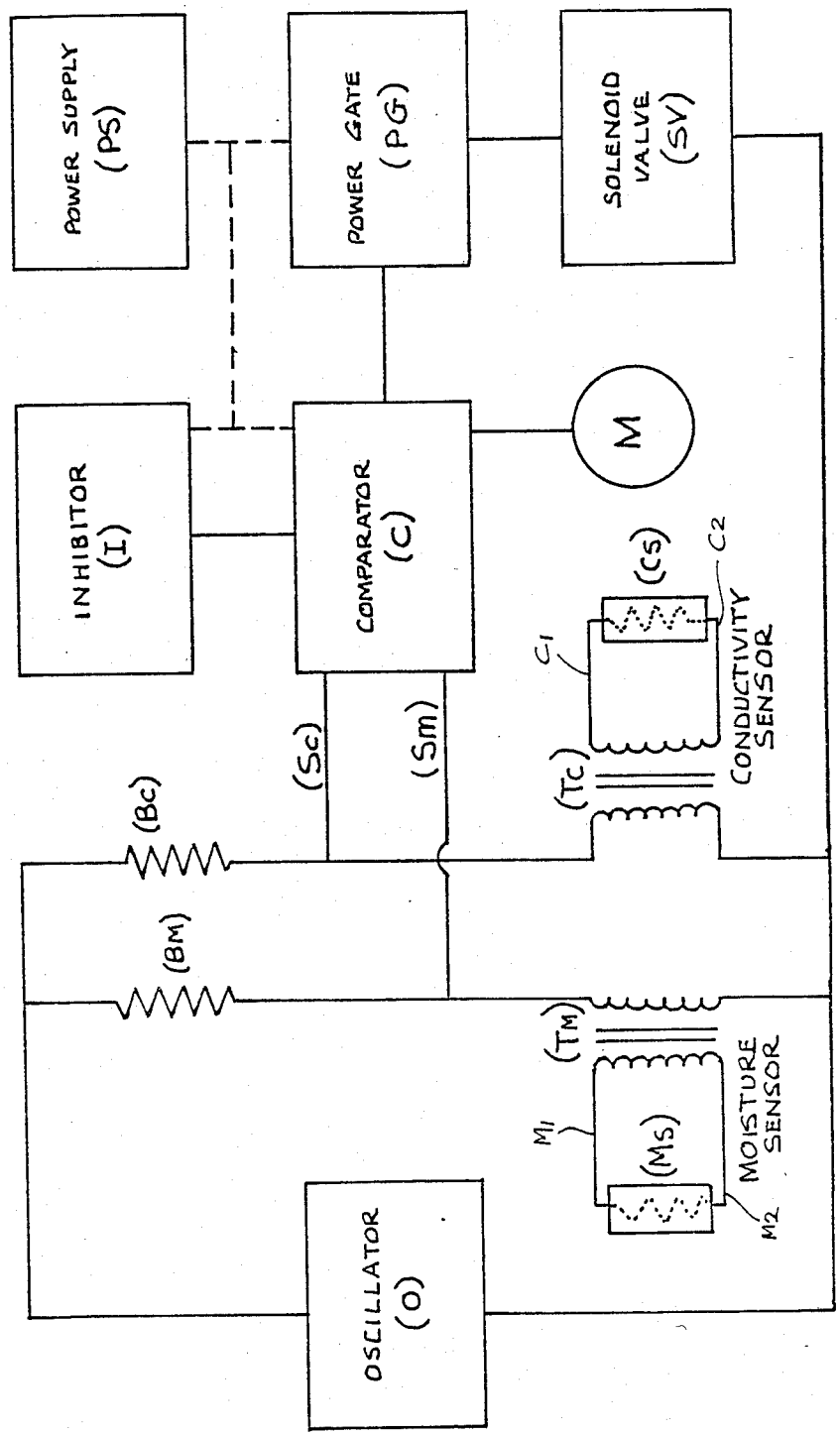
FIG. 4 is a schematic block circuit diagram illustrating a preferred form of control means for the respective sensing elements.

The sensing element illustrated in FIGS. 1a, 1b and 1c comprises a pair of sensor zones (Ms) and (Cs) constructed in the form of a rectangular prismatic block (b) adapted to be placed in the ground in the area requiring surveillance. The block (b) is conveniently produced from a porous ceramic material having a substantially controlled pore size. It will of course be appreciated that materials other than ceramics could be used for the block structure (b). The porous structure of the block (b) is such as to allow ground or soil moisture to be absorbed therein when it is located in a position of use. Within the block (b) in the region of the first zone (Ms) is a pair of electrode elements (em1 and em2). These electrode elements are formed by packing graphite or other similarly conductive powder into spaced bore holes within the block (b) and thereafter electrically insulated conducting wires (M1) and (M2) pass through the block and outwardly to the control circuit (FIG. 4). An insulating and sealing region S2 maintains the electrodes elements (em1) and (em2) in close contact with the porous block (b) and insulated and spaced from the second sensor zone (Cs).

The second sensor zone (Cs) is formed by a substantially rectangular cavity (f) in the block (b) located between the sealing region (S2) and a second or end insulating and sealing region (S1). Two sensing electrode elements (ec1) and (ec2) are arranged within the cavity (f) at spaced locations and the cavity is filled with a fine electrically insulating powder (P). The powder (P) provides a second porous zone with a mean pore size (Pmc) which is substantially less than the mean pore size (Pmm) of the block (b) in the first sensor zone (Ms). Appropriately, insulated conductors (C1) and (C2) provide electrical contact with the electrode elements (ec1) and (ec2) and connect these elements with the control circuit (FIG. 4).

Reference will now be made to the alternative constructions illustrated in FIGS. 2 and 3. In the embodiment of FIG. 2 the first sensor zone (Ms) is depicted at one end of a mounting block 10 with the second sensor zone (Cs) arranged at the other end of the mounting block 10. Both sensor zones (Ms) and (CS) are conveniently made from porous ceramic materials which may be extruded in the form of a rectangular bar and cut off into plates 11 and 12 as shown in FIG. 2. The mean pore size (Pmm) of the plate 11 is substantially greater and preferably between one and one-half and five times greater, than the mean pore size (Pmc) of the plate 12. The physical construction of the sensors (Ms) and (C2) are essentially the same and therefore only the sensor (Ms) is hereinafter described.

Referring to FIG. 2, the sensor (Ms) comprises the porous ceramic plate 11 with conducting electrode elements (em1) and (em2) coated onto opposite sides of the ceramic plate 11. Furthermore, electrically insulated conductors (M1) and (M2) connected the electrode elements (em1) and (em2) to the control circuit (FIG. 4). Each of the electrode elements are further covered by an insulating layer 13 and 14 which may be formed by an epoxy resin coating or the like. The layers 13 and 14 leave sufficient free contact area for the porous plate 11 to absorb water from ground contact.

FIG. 3 illustrates a third alternative construction of a sensing element comprising a porous block 20 having sensor (Ms) and (Cs) arranged therein. The sensors each have a pair of electrodes (em1), (em2) and (ec1), (ec2) connected by electrical wiring (M1), (M2) and (C1), (C2) to the control circuit (FIG. 4). The electrodes are arranged transversely extending through the block 20 with the electrodes (em1), (em2) forming an electric circuit path through the porous block 20. The electrode (ec1), (ec2) are arranged to complete an electric circuit path through a second porous zinc 21 surrounding the electrodes. As with the other embodiments the mean pore size (Pmm) of the block 20 is substantially greater, and of the order of one and one half to five times greater, than the mean pore size (Pmc) of the zone 21.

The control device, principally illustrated in FIG. 4 is capable of use with all of the above described embodiments. The control circuitry may form part of the sensing element, or may be arranged as a separate control element located at some suitable control point away from the actual use site of the sensing element.

The circuit diagram illustrated in FIG. 4 demonstrates a preferred form of control means for the present invention. The circuit includes an oscillator (O) providing an alternating voltage across a bridge circuit comprising burden resistors (BM) and (BC) on two adjacent arms and the primary windings of transformer means (TM) and (TC) on the other two adjacent arms. The secondary windings of the transformer of the transformer means (TM) is connected by the conductor elements (M1) and (M2) to the electrodes (em1) and (em2) of the sensor zone (Ms) of the sensing element. Similarly, the secondary winding of the transformer means (TC) is connected by the conductor elements (C1) and (C2) to the electrodes (ec1) and (ec2) of the second sensor zone (Cs) of the sensing element.

As the moisture in the porous material in the sensor zone Ms decreases so impedance in the primary windings of the transformer, (TM) will be caused to increase. Similarly, if moisture in the sensor zone Ms increases, impedance in the primary winding of transformer (TM) will be caused to decrease. A bridge imbalance is therefore caused on change of moisture within the block thereby increasing or decreasing the voltage signal (SM).

If conductivity of the moisture within the sensor zone (Cs) increases, for example, as a result of increased dissolved salts, impedance in the primary winding of the transformer (TC) will decrease. The reverse will occur should the conductivity decrease. This will provide a bridge compensation on the change in moisture conductivity sensed by (Ms).

In a situation where the moisture in the sensor zone (Ms) decreased, the voltage signal (SM) exceeds the compensation or signal (SC) the comparator (C) may cause a signal to pass to the power gate (PG) which causes the solenoid valve (SV) to become energised permitting water to flow in a water control and supply circuit (not shown) to the area monitored by the sensor.

On increase in moisture level within the block (b) the process is reversed and terminates energy to the solenoid valve (SV) as the voltage signal (SM) falls below signal (SC).

The comparator (C) may be arranged to provide signals of $K_1X$ (SM/SC) and $K_2X$ (SC) to indicating meters such as (M) to provide visual indication of moisture level and solubles concentrations respectively. $K_1$ and $K_2$ being costants for the apparatus concerned.

An inhibitor (I) may be provided to arrest the signal from the comparator to the power gate. The inhibitor may be operated in response to a time control, light or any other factor which may be relevant.

I claim:

1. A moisture sensing assembly comprising a body having therein a first zone formed of porous material with a first range of pore size having a first mean pore size and a second zone formed of a porous material with a second range of pore size having a second mean pore size such that in use said body is located within a desired soil area under surveillance whereby both said first and second zones are placed in hydraulic conduction with the desired soil area, said first mean pore size being substantially greater than said second mean pore size such that the second zone will remain hydrated when the first zone is becoming dehydrated, and control means associated with each of said first and second zones for sensing an electrical property of each of said zones, said control means including electrode elements associated with each of said first and second zones in spaced relation and defining therebetween a respective electric current flow path through each of said first and second zones, said control means further including a magnetic coupling means for electrically isolating respective pairs of said electrode elements to thereby define electric current flow paths through said respective first and second zones.

2. A sensing assembly according to claim 1 wherein the first and second zones are formed from the same material.

3. A sensing assembly according to claim 2, wherein the first and second zones are formed from ceramics material.

4. A sensing assembly according to claim 1 wherein the first and second zones are formed from different materials.

5. A sensing assembly according to claim 4 wherein one of said first or second zones is formed of a ceramic material and the other of said first or second zones is formed of particulate material.

6. A sensing assembly according to claim 1 wherein the mean pore size of the first zone is at least one and one half times greater than the mean pore size of the second zone.

7. A sensing assembly according to claim 6 wherein the pore size of said first zone is up to five times greater than the mean pore size of the second zone.

8. A sensing assembly according to claim 1 wherein the pore size of each of said first and/or second zones is controlled to lie between limits predetermined for each zone.

9. A sensing assembly according to claim 8 wherein the pore size of said first zone is substantially uniform and the pore size of the second zone is substantially uniform.

10. A sensing assembly according to claim 1 wherein the primary winding of each said transformer means forming adjacent arms of a bridge circuit.

11. A sensing assembly according to claim 10 including an oscillator providing an alternating voltage across the bridge circuit, said bridge circuit providing output signals from each of said transformer means to a comparator, and said comparator providing at least one control signal.

12. A sensing assembly according to claim 1 wherein at least a part of the outer surface of said body is substantially formed by said porous material forming said first zone and having the first mean pore size.

13. A sensing assembly according to claim 12 wherein said second zone is formed wholly within said porous material forming said first zone.

14. A sensing assembly according to claim 1 wherein said magnetic isolating means comprises a separate secondary winding of a transformer means connected across each said pair of electrode elements defining an electric current flow through said respective first and second zones.

* * * * *